United States Patent
Gu et al.

(10) Patent No.: US 10,634,676 B2
(45) Date of Patent: Apr. 28, 2020

(54) METHOD AND KIT FOR SIMULTANEOUSLY DETECTING HUMAN PARVOVIRUS B19 ANTIGEN AND ANTIBODY

(71) Applicant: FUJIREBIO INC., Tokyo (JP)

(72) Inventors: Ran Gu, Tokyo (JP); Atsushi Kaneko, Tokyo (JP); Katsumi Aoyagi, Tokyo (JP)

(73) Assignee: FUJIREBIO INC., Tokyo (JP)

( * ) Notice: Subject to any disclaimer, the term of this patent is extended or adjusted under 35 U.S.C. 154(b) by 0 days.

(21) Appl. No.: 15/768,112

(22) PCT Filed: Oct. 14, 2016

(86) PCT No.: PCT/JP2016/080507
§ 371 (c)(1),
(2) Date: Sep. 7, 2018

(87) PCT Pub. No.: WO2017/065261
PCT Pub. Date: Apr. 20, 2017

(65) Prior Publication Data
US 2018/0364231 A1   Dec. 20, 2018

(30) Foreign Application Priority Data
Oct. 15, 2015   (JP) .................................. 2015-203432

(51) Int. Cl.
| | | |
|---|---|---|
| *C07K 14/005* | (2006.01) | |
| *C07K 14/015* | (2006.01) | |
| *A61K 39/00* | (2006.01) | |
| *C07K 16/08* | (2006.01) | |
| *C12N 15/864* | (2006.01) | |
| *G01N 33/569* | (2006.01) | |
| *G01N 33/53* | (2006.01) | |
| *C12N 15/09* | (2006.01) | |
| *C12N 15/02* | (2006.01) | |

(52) U.S. Cl.
CPC ... *G01N 33/56983* (2013.01); *G01N 33/5306* (2013.01); *C12N 15/02* (2013.01); *C12N 15/09* (2013.01); *G01N 2333/015* (2013.01); *G01N 2469/10* (2013.01); *G01N 2469/20* (2013.01); *G01N 2800/26* (2013.01)

(58) Field of Classification Search
CPC .... C07K 14/005; C07K 16/081; A61K 39/00; C12N 15/86; C12N 2710/14043
See application file for complete search history.

(56) References Cited

U.S. PATENT DOCUMENTS

| | | | | |
|---|---|---|---|---|
| 6,479,641 B2 * | 11/2002 | Whelihan | ......... | G01N 33/56983 424/147.1 |
| 7,445,889 B2 * | 11/2008 | Smith-Norowitz | | ......................... G01N 33/56983 435/235.1 |
| 2002/0173493 A1 | 11/2002 | Aoyagi et al. | | |
| 2004/0072267 A1 | 4/2004 | Rieunier et al. | | |

FOREIGN PATENT DOCUMENTS

| | | | |
|---|---|---|---|
| EP | 1806363 | * | 7/2007 |
| EP | 1806363 | * | 9/2013 |
| JP | 8-304397 A | | 11/1996 |
| JP | 2006-501151 A | | 1/2006 |
| JP | 2008-145181 A | | 6/2008 |
| WO | WO 00/07023 A1 | | 2/2000 |

OTHER PUBLICATIONS

International Search Report (PCT/ISA/210) issued in PCT/JP2016/080507, dated Jan. 10, 2017.
Written Opinion (PCT/ISA/237) issued in PCT/JP2016/080507, dated Jan. 10, 2017.

* cited by examiner

*Primary Examiner* — Barry A Chestnut
(74) *Attorney, Agent, or Firm* — Birch, Stewart, Kolasch & Birch, LLP

(57) ABSTRACT

Disclosed is a novel means of simultaneously detecting a human parvovirus B19 antigen and an IgM type anti-human parvovirus B19 antibody. The method of simultaneously detecting a human parvovirus B19 antigen and an IgM type anti-human parvovirus B19 antibody in a sample according to the present invention comprises bringing a sample into contact with (1) a 1st probe for detecting the parvovirus B19 antigen and (2) a 2nd probe for detecting the IgM type anti-parvovirus B19 antibody in the presence of a surfactant within the same reaction.

15 Claims, No Drawings
Specification includes a Sequence Listing.

SEQUENCE LISTING

```
<160> NUMBER OF SEQ ID NOS: 2

<210> SEQ ID NO 1
<211> LENGTH: 554
<212> TYPE: PRT
<213> ORGANISM: Parvovirus B19

<400> SEQUENCE: 1

Met Thr Ser Val Asn Ser Ala Glu Ala Ser Thr Gly Ala Gly Gly Gly
1               5                   10                  15

Gly Ser Asn Pro Val Lys Ser Met Trp Ser Glu Gly Ala Thr Phe Ser
                20                  25                  30

Ala Asn Ser Val Thr Cys Thr Phe Ser Arg Gln Phe Leu Ile Pro Tyr
            35                  40                  45

Asp Pro Glu His His Tyr Lys Val Phe Ser Pro Ala Ala Ser Ser Cys
        50                  55                  60

His Asn Ala Ser Gly Lys Glu Ala Lys Val Cys Thr Ile Ser Pro Ile
65                  70                  75                  80

Met Gly Tyr Ser Thr Pro Trp Arg Tyr Leu Asp Phe Asn Ala Leu Asn
                85                  90                  95

Leu Phe Phe Ser Pro Leu Glu Phe Gln His Leu Ile Glu Asn Tyr Gly
            100                 105                 110

Ser Ile Ala Pro Asp Ala Leu Thr Val Thr Ile Ser Glu Ile Ala Val
        115                 120                 125

Lys Asp Val Thr Asp Lys Thr Gly Gly Gly Val Gln Val Thr Asp Ser
    130                 135                 140
```

```
Thr Thr Gly Arg Leu Cys Met Leu Val Asp His Glu Tyr Lys Tyr Pro
145                 150                 155                 160

Tyr Val Leu Gly Gln Gly Gln Asp Thr Leu Ala Pro Glu Leu Pro Ile
            165                 170                 175

Trp Val Tyr Phe Pro Pro Gln Tyr Ala Tyr Leu Thr Val Gly Asp Val
                180                 185                 190

Asn Thr Gln Gly Ile Ser Gly Asp Ser Lys Lys Leu Ala Ser Glu Glu
            195                 200                 205

Ser Ala Phe Tyr Val Leu Glu His Ser Ser Phe Gln Leu Leu Gly Thr
        210                 215                 220

Gly Gly Thr Ala Thr Met Ser Tyr Lys Phe Pro Pro Val Pro Pro Glu
225                 230                 235                 240

Asn Leu Glu Gly Cys Ser Gln His Phe Tyr Glu Met Tyr Asn Pro Leu
                245                 250                 255

Tyr Gly Ser Arg Leu Gly Val Pro Asp Thr Leu Gly Gly Asp Pro Lys
            260                 265                 270

Phe Arg Ser Leu Thr His Glu Asp His Ala Ile Gln Pro Gln Asn Phe
        275                 280                 285

Met Pro Gly Pro Leu Val Asn Ser Val Ser Thr Lys Glu Gly Asp Ser
290                 295                 300

Ser Asn Thr Gly Ala Gly Lys Ala Leu Thr Gly Leu Ser Thr Gly Thr
305                 310                 315                 320

Ser Gln Asn Thr Arg Ile Ser Leu Arg Pro Gly Pro Val Ser Gln Pro
                325                 330                 335

Tyr His His Trp Asp Thr Asp Lys Tyr Val Thr Gly Ile Asn Ala Ile
            340                 345                 350

Ser His Gly Gln Thr Thr Tyr Gly Asn Ala Glu Asp Lys Glu Tyr Gln
        355                 360                 365

Gln Gly Val Gly Arg Phe Pro Asn Glu Lys Glu Gln Leu Lys Gln Leu
    370                 375                 380

Gln Gly Leu Asn Met His Thr Tyr Phe Pro Asn Lys Gly Thr Gln Gln
385                 390                 395                 400

Tyr Thr Asp Gln Ile Glu Arg Pro Leu Met Val Gly Ser Val Trp Asn
                405                 410                 415

Arg Arg Ala Leu His Tyr Glu Ser Gln Leu Trp Ser Lys Ile Pro Asn
            420                 425                 430

Leu Asp Asp Ser Phe Lys Thr Gln Phe Ala Ala Leu Gly Gly Trp Gly
        435                 440                 445

Leu His Gln Pro Pro Gln Ile Phe Leu Lys Ile Leu Pro Gln Ser
    450                 455                 460

Gly Pro Ile Gly Gly Ile Lys Ser Met Gly Ile Thr Thr Leu Val Gln
465                 470                 475                 480

Tyr Ala Val Gly Ile Met Thr Val Thr Met Thr Phe Lys Leu Gly Pro
                485                 490                 495

Arg Lys Ala Thr Gly Arg Trp Asn Pro Gln Pro Gly Val Tyr Pro Pro
            500                 505                 510

His Ala Ala Gly His Leu Pro Tyr Val Leu Tyr Asp Pro Thr Ala Thr
        515                 520                 525

Asp Ala Lys Gln His His Arg His Gly Tyr Glu Lys Pro Glu Glu Leu
    530                 535                 540

Trp Thr Ala Lys Ser Arg Val His Pro Leu
545                 550
```

<210> SEQ ID NO 2
<211> LENGTH: 5594
<212> TYPE: DNA
<213> ORGANISM: Parvovirus B19

<400> SEQUENCE: 2

| | | | | | |
|---|---|---|---|---|---:|
| ccaaatcaga | tgccgccggt | cgccgccggt | aggcgggact | tccggtacaa | gatggcggac | 60 |
| aattacgtca | tttcctgtga | cgtcatttcc | tgtgacgtca | cttccggtgg | gcgggacttc | 120 |
| cggaattagg | gttggctctg | gccagcttg | cttggggttg | ccttgacact | aagacaagcg | 180 |
| gcgcgccgct | tgtcttagtg | gcacgtcaac | cccaagcgct | ggcccagagc | caaccctaat | 240 |
| tccggaagtc | ccgcccaccg | gaagtgacgt | cacaggaaat | gacgtcacag | gaaatgacgt | 300 |
| aattgtccgc | catcttgtac | cggaagtccc | gcctaccggc | ggcgaccggc | ggcatctgat | 360 |
| ttggtgtctt | cttttaaatt | ttagcgggct | tttttcccgc | cttatgcaaa | tgggcagcca | 420 |
| ttttaagtgt | tttactataa | ttttattggt | cagttttgta | acggttaaaa | tgggcggagc | 480 |
| gtaggcgggg | actacagtat | atatagcacg | gcactgccgc | agctctttct | ttctgggctg | 540 |
| cttttttcctg | gactttcttg | ctgtttttg | tgagctaact | aacaggtatt | tatactactt | 600 |
| gttaacatac | taacatggag | ctatttagag | gggtgcttca | agtttcttct | aatgttctgg | 660 |
| actgtgctaa | cgataactgg | tggtgctctt | tactggattt | agacacttct | gactgggaac | 720 |
| cactaactca | tactaacaga | ctaatggcaa | tatacttaag | cagtgtggct | tctaagcttg | 780 |
| actttaccgg | ggggccacta | gcagggtgct | tgtactttt | tcaagtagaa | tgtaacaaat | 840 |
| ttgaagaagg | ctatcatatt | catgtggtta | ttgggggggcc | agggttaaac | cccagaaacc | 900 |
| tcacagtgtg | tgtagagggg | ttatttaata | atgtacttta | tcaccttgta | actgaaaatg | 960 |
| taaagctaaa | attttttgcca | ggaatgacta | caaaaggcaa | atactttaga | gatggagagc | 1020 |
| agtttataga | aaactattta | atgaaaaaaa | tacctttaaa | tgttgtatgg | tgtgttacta | 1080 |
| atattgatgg | atatatagat | acctgtattt | ctgctacttt | tagaaggga | gcttgccatg | 1140 |
| ccaagaaacc | ccgcattacc | acagccataa | atgatactag | tagtgatgct | ggggagtcta | 1200 |
| gcggcacagg | ggcagaggtt | gtgccatttta | atgggaaggg | aactaaggct | agcataaagt | 1260 |
| ttcaaactat | ggtaaactgg | ttgtgtgaaa | acagagtgtt | tacagaggat | aagtggaaac | 1320 |
| tagttgactt | taaccagtac | actttactaa | gcagtagtca | cagtggaagt | tttcaaattc | 1380 |
| aaagtgcact | aaaaactagca | atttataaag | caactaattt | agtgcctact | agcacatttt | 1440 |
| tattgcatac | agactttgag | caggttatgt | gtattaaaga | caataaaatt | gttaaattgt | 1500 |
| tactttgtca | aaactatgac | ccctatttgg | tggggcagca | tgtgttaaag | tggattgata | 1560 |
| aaaaatgtgg | caagaaaaat | acactgtggt | tttatgggcc | gccaagtaca | ggaaaaacaa | 1620 |
| acttggcaat | ggccattgct | aaaagtgttc | cagtatatgg | catggttaac | tggaataatg | 1680 |
| aaaactttcc | atttaatgat | gtagcaggga | aaagcttggt | ggtctgggat | gaaggtatta | 1740 |
| ttaagtctac | aattgtagaa | gctgcaaaag | ccatttttagg | cgggcaaccc | accagggtag | 1800 |
| atcaaaaaat | gcgtggaagt | gtagctgtgc | ctggagtacc | tgtggttata | accagcaatg | 1860 |
| gtgacattac | ttttgttgta | agcgggaaca | ctacaacaac | tgtacatgct | aaagcccttaa | 1920 |
| aagagcgcat | ggtaaagtta | aactttactg | taagatgcag | ccctgacatg | gggttactaa | 1980 |
| cagaggctga | tgtacaacag | tggcttacat | ggtgtaatgc | acaaagctgg | gaccactatg | 2040 |
| aaaactgggc | aataaaactac | acttttgatt | tccctgaat | taatgcagat | gccctccacc | 2100 |
| cagacctcca | aaccacccca | attgtcacag | acaccagtat | cagcagcagt | ggtggtgaaa | 2160 |

```
gctctgaaga actcagtgaa agcagctttt ttaacctcat caccccaggc gcctggaaca    2220
ctgaaacccc gcgctctagt acgcccatcc ccgggaccag ttcaggagaa tcatttgtcg    2280
gaagcccagt ttcctccgaa gttgtagctg catcgtggga agaagccttc tacacacctt    2340
tggcagacca gtttcgtgaa ctgttagttg gggttgatta tgtgtgggac ggtgtaaggg    2400
gtttacctgt gtgttgtgtg caacatatta acaatagtgg gggaggcttg ggactttgtc    2460
cccattgcat taatgtaggg gcttggtata atggatggaa atttcgagaa tttaccccag    2520
atttggtgcg atgtagctgc catgtgggag cttctaatcc cttttctgtg ctaacctgca    2580
aaaaatgtgc ttacctgtct ggattgcaaa gctttgtaga ttatgagtaa agaaagtggc    2640
aaatggtggg aaagtgatga taaatttgct aaagctgtgt atcagcaatt tgtggaattt    2700
tatgaaaagg ttactggaac agacttagag cttattcaaa tattaaaaga tcattataat    2760
atttctttag ataatcccct agaaaaccca tcctctctgt ttgacttagt tgctcgtatt    2820
aaaaataacc ttaaaaactc tccagactta tatagtcatc attttcaaag tcatggacag    2880
ttatctgacc accccccatgc cttatcatcc agtagcagtc atgcagaacc tagaggagaa    2940
aatgcagtat tatctagtga agacttacac aagcctgggc aagttagcgt acaactaccc    3000
ggtactaact atgttgggcc tggcaatgag ctacaagctg gcccccgca aagtgctgtt    3060 gacagtgctg caaggattca tgactttagg tatagccaac tggctaagtt gggaataaat    3120
ccatatactc attggactgt agcagatgaa gagcttttaa aaatataaa aatgaaact    3180 gggtttcaag cacaagtagt aaaagactac tttactttaa aaggtgcagc tgcccctgtg    3240
gcccattttc aaggaagttt gccggaagtt cccgcttaca acgcctcaga aaaataccca    3300
agcatgactt cagttaattc tgcagaagcc agcactggtg caggaggggg gggcagtaat    3360
cctgtcaaaa gcatgtggag tgaggggggcc acttttagtg ccaactctgt aacttgtaca    3420
ttttccagac agttttaat tccatatgac ccagagcacc attataaggt gttttctccc    3480
gcagcaagta gctgccacaa tgccagtgga aaggaggcaa aggtttgcac cattagtccc    3540
ataatgggat actcaacccc atggagatat ttagatttta atgctttaaa tttattttt    3600 tcacctttag agtttcagca cttaattgaa aattatggaa gtatagctcc tgatgcttta    3660
actgtaacca tatcagaaat tgctgttaag gatgttacag acaaaactgg agggggggta    3720
caggttactg acagcactac agggcgccta tgcatgttag tagaccatga atacaagtac    3780
ccatatgtgt tagggcaagg tcaggatact ttagccccag aacttcctat ttgggtatac    3840
tttccccctc aatatgctta cttaacagta ggagatgtta acacacaagg aatttctgga    3900
gacagcaaaa aattagcaag tgaagaatca gcattttatg ttttggaaca cagttctttt    3960
cagcttttag gtacaggagg tacagcaact atgtcttata agtttcctcc agtgccccca    4020
gaaaatttag agggctgcag tcaacacttt tatgaaatgt acaatcccTT ATACGGATCC    4080

CGCTTAGGGG TTCCTGACAC ATTAGGAGGT GACCCAAAAT TTAGATCTTT AACACATGAA    4140

GACCATGCAA TTCAGCCCCA AAACTTCATG CCAGGGCCAC TAGTAAACTC AGTGTCTACA    4200

AAGGAGGGAG ACAGCTCTAA TACTGGAGCT GGAAAAGCCT TAACAGGCCT TAGCACAGGT    4260

ACCTCTCAAA ACACTAGAAT ATCCTTACGC CCTGGGCCAG TGTCTCAGCC ATACCACCAC    4320

TGGGACACAG ATAAATATGT CACAGGAATA AATGCCATTT CTCATGGTCA GACCACTTAT    4380

GGTAACGCTG AAGACAAAGA GTATCAGCAA GGAGTGGGTA GATTTCCAAA TGAAAAAGAA    4440

CAGCTAAAAC AGTTACAGGG TTTAAACATG CACACCTATT TCCCAATAA AGGAACCCAG    4500
```

```
caatatacag atcaaattga gcgccccta  atggtgggtt ctgtatggaa cagaagagcc  4560
cttcactatg aaagccagct gtggagtaaa attccaaatt tagatgacag ttttaaaact  4620
cagtttgcag ccttaggagg atggggtttg catcagccac ctcctcaaat atttttaaaa  4680
atattaccac aaagtgggcc aattggaggt attaaatcaa tgggaattac taccttagtt  4740
cagtatgccg tgggaattat gacagtaact atgacattta aattggggcc ccgtaaagct  4800
acgggacggt ggaatcctca acctggagta tatccccgc  acgcagcagg tcatttacca   4860
tatgtactat atgacccac  agctacagat gcaaaacaac accacagaca tggatatgaa   4920
aagcctgaag aattgtggac agccaaaagc cgtgtgcacc cattgtaaac actccccacc  4980
gtgccctcag ccaggatgcg taactaaacg cccaccagta ccaccagac  tgtacctgcc   5040 ccctcctgta cctataagac agcctaacac aaaagatata gacaatgtag aatttaagta  5100
cttaaccaga tatgaacaac atgttattag aatgttaaga ttgtgtaata tgtatcaaaa  5160
tttagaaaaa taaacatttg ttgtggttaa aaaattatgt tgttgcgctt taaaaattta  5220
aaagaagaca ccaaatcaga tgccgccggt cgccgccggt aggcgggact tccggtacaa  5280
gatggcggac aattacgtca tttcctgtga cgtcatttcc tgtgacgtca cttccggtgg  5340
gcgggacttc cggaattagg gttggctctg ggccagcgct tggggttgac gtgccactaa  5400
gacaagcggc gcgccgcttg tcttagtgtc aaggcaaccc caagcaagct ggcccagagc  5460
caaccctaat tccggaagtc ccgcccaccg gaagtgacgt cacaggaaat gacgtcacag  5520
gaaatgacgt aattgtccgc catcttgtac cggaagtccc gcctaccggc ggcgaccggc  5580
ggcatctgat ttgg                                                    5594
```

METHOD AND KIT FOR SIMULTANEOUSLY DETECTING HUMAN PARVOVIRUS B19 ANTIGEN AND ANTIBODY

TECHNICAL FIELD

The present invention relates to a method of simultaneously detecting a human parvovirus B19 antigen and antibody contained in a sample, and a kit for simultaneous detection of a human parvovirus B19 antigen and antibody.

BACKGROUND ART

Human parvovirus B19 is a linear single-stranded DNA virus classified into *Parvoviridae Parvovirus*. The virus particle has an icosahedral structure, in which the capsid proteins VP1 (83 kDa) and VP2 (58 kDa) at a ratio of 1:9 constitute a capsid. The virus has no envelope. As diseases and symptoms caused by infection with parvovirus B19, erythema infectiosum (slapped cheek disease), arthritis, fetal hydrops, abortion, and the like are known.

Since one attack of human parvovirus B19 gives a person lifelong immunity, a new infection cannot be evaluated by measurement of the IgG type antibody. Accordingly, it is common to measure the IgM type antibody in order to evaluate a new infection with human parvovirus B19.

Examples of the known method of immunologically measuring human parvovirus B19 in a sample include not only an immunoassay method for an IgM type anti-human parvovirus B19 antibody, but also an immunoassay method using an anti-parvovirus B19 antibody subsequent to pretreating a sample under the condition of pH 4.0 or less (Patent Document 1), and an immunoassay method using an anti-parvovirus B19 antibody subsequent to pretreating a sample with guanidine at pH 4.5 to 6.5 (Patent Document 2). In these methods, antibodies contained in a sample are inactivated.

Also known is a method of detecting parvovirus B19 at high sensitivity by combined use of the results from an immunoassay of a parvovirus B19 antigen and the results from an immunoassay of an IgM antibody against parvovirus B19 (Patent Document 3).

On the other hand, a method of simultaneously detecting a human hepatitis C virus (HCV) antigen and an IgG type anti-HCV antibody in a sample (Patent Document 4), and a method of simultaneously detecting a human immunodeficiency virus (HIV) antigen and an IgG type anti-HIV antibody (Patent Document 5) are known.

PRIOR ART DOCUMENT(S)

Patent Document(s)

Patent Document 1: JP 2001-343388 A
Patent Document 2: JP 2007-278902 A
Patent Document 3: JP 2008-145181 A
Patent Document 4: WO00/007023
Patent Document 5: JP 2001-504572 A

SUMMARY OF THE INVENTION

Problem to be Solved by the Invention

In the initial phase of an infection with parvovirus B19, there is a period during which no anti-parvovirus B19 antibody (IgM) is detected in blood (window period). In this window period, detection of a parvovirus B19 antigen makes it possible to detect parvovirus B19 at an early stage. On the other hand, when the titer of blood parvovirus B19 antigen is low, parvovirus B19 can be detected at a higher sensitivity by detecting an IgM type antibody. Thus, it is desirable to detect both a parvovirus B19 antigen and an IgM type anti-parvovirus B19 antibody.

Patent Document 3 discloses combined use of the results of an immunoassay of a parvovirus B19 antigen and the results of an immunoassay of an IgM type antibody. This method requires separate measurements of the antigen and the antibody, and thus requires a large quantity of samples. In addition, this method requires two different immunoassays, taking some labor and time.

Patent Documents 4 and 5 disclose antigen-antibody simultaneous measurement methods for HCV and HIV. HCV and HIV have an envelope, and in these methods antigens in the envelope are detected. Therefore, it is necessary in these methods to break down the envelope membrane protein and expose antigens from inside the envelope. Furthermore, the antibody measured in the methods of the Patent Documents is an IgG type antibody. Generally, IgM antibodies tend to have lower stability than IgG antibodies; that is, the immunoassay conditions described in the methods of these Patent Documents are to simultaneously measure an IgG type antibody and an antigen inside the envelope, which envelope should be exposed by breaking down the envelope membrane protein. Thus, these conditions cannot be applied to a simultaneous detection system for an antigen of parvovirus B19, which does not have an envelope, and an IgM type antibody.

An object of the present invention is to provide a means for simultaneously detecting a human parvovirus B19 antigen and an IgM type anti-human parvovirus B19 antibody.

Means for Solving the Problems

The present inventors have diligently studied an immunoassay system for simultaneously detecting a human parvovirus B19 antigen and an IgM type anti-human parvovirus B19 antibody to find that addition of a specific surfactant to an antigen-antibody reaction solution makes it possible to simultaneously detect a parvovirus B19 antigen and an IgM type anti-parvovirus B19 antibody at high sensitivity, thereby completing the present invention.

That is, the present invention provides a method of simultaneously detecting at least one parvovirus B19 antigen and at least one IgM type anti-parvovirus B19 antibody present in a sample, the method comprising bringing the sample into contact with
(1) a 1st probe for detecting the parvovirus B19 antigen, and
(2) a 2nd probe for detecting the IgM type anti-parvovirus B19 antibody, in the presence of a surfactant within the same reaction. The present invention also provides a kit for simultaneous detection of a parvovirus B19 antigen and an IgM type anti-parvovirus B19 antibody, which is used in the method according to the above-described present invention and comprises a 1st probe for detecting a parvovirus B19 antigen, a 2nd probe for detecting an IgM type anti-parvovirus B19 antibody, and a surfactant.

Effect of the Invention

The present invention makes it possible to simultaneously detect at least one parvovirus B19 antigen and at least one IgM type anti-parvovirus B19 antibody which are present in a sample, and accordingly, to detect whether the sample is positive for parvovirus B19 or not at high sensitivity by simple operation.

MODE FOR CARRYING OUT THE INVENTION

The method for simultaneous detection of the parvovirus B19 antigen and antibody according to the present invention is a method of simultaneously detecting at least one parvovirus B19 antigen and at least one IgM type anti-parvovirus B19 antibody which are present in a sample, and comprises bringing the sample into contact with
(1) a 1st probe for detecting the parvovirus B19 antigen, and
(2) a 2nd probe for detecting the human IgM type anti-parvovirus B19 antibody, in the presence of a surfactant within the same reaction. The term "within the same reaction" means that the sample is allowed to react with the 1st probe and the 2nd prove in the same reaction solution (for example, in the same well, in the same reaction cell, and the like).

The surfactant is required to be present at least in the reaction system in which the sample reacts with the 1st probe and the 2nd probe. In other reaction steps (for example, a secondary reaction step in a sandwich immunoassay), a surfactant may be present or absent.

The surfactant is not limited to a particular kind and may be any of those which enhance sensitivity in a parvovirus B19 antigen-antibody simultaneous detection system. For example, at least one surfactant selected from an anionic surfactant, an amphoteric surfactant, and a cationic surfactant is preferably used. One kind of surfactant may be used, or multiple kinds of surfactants may be used in combination. The surfactant may also be used in combination with another additive and the like. A surfactant which enhances sensitivity in a parvovirus B19 antigen-antibody simultaneous detection system may be at least one selected from an anionic surfactant and an amphoteric surfactant. When used singly, a nonionic surfactant such as a Tween-series surfactant or a Triton (registered trademark)-series surfactant does not have an effect to increase sensitivity in a parvovirus B19 antigen-antibody simultaneous detection system (see, Example (12) described below), but may be used as another additive, for example, for different purposes, in combination with a surfactant which increases sensitivity in a parvovirus B19 antigen-antibody simultaneous detection system.

Preferred examples of the anionic surfactant include those having an alkyl group comprising 9 or more carbon atoms, more preferably 11 or more carbon atoms, in the molecule. The alkyl group is preferably a linear alkyl group. Examples of the anionic surfactant having an alkyl group comprising 9 or more carbon atoms include: alkyl sulfuric ester salts such as sodium dodecyl sulfate (SDS); N-acyl sarcosine salts such as sodium N-decanoyl sarcosinate (NDS), sodium N-lauroyl sarcosinate (NLS), and sodium N-myristoyl sarcosinate; alkylbenzenesulfonic acid salts such as dodecylbenzenesulfonate (SBDS); and the like.

Preferred examples of the amphoteric surfactant include those which have an alkyl group comprising 10 or more carbon atoms, more preferably 12 or more carbon atoms, and have a quaternary ammonium in the molecule. The alkyl group is preferably a linear alkyl group. Preferred examples of the amphoteric surfactant which has an alkyl group comprising 10 or more carbon atoms and has a quaternary ammonium include amphoteric surfactants having a structure represented by $CH_3-(CH_2)_n-N^+(CH_3)_2-[(CH_2)_3-SO_3^-]$ (n is an integer of 9 or greater), specific examples of which include N-decyl-N,N-dimethyl-3-ammonio-1-propanesulfonate (C10APS), N-dodecyl-N,N-dimethyl-3-ammonio-1-propanesulfonate (C12APS), N-tetradecyl-N,N-dimethyl-3-ammonio-1-propanesulfonate (C14APS), N-hexadecyl-N,N-dimethyl-3-ammonio-1-propanesulfonate (C16APS), and the like.

Preferred examples of the cationic surfactant include those which have an alkyl group comprising 10 or more carbon atoms, more preferably 12 or more carbon atoms, and have a quaternary ammonium in the molecule. The alkyl group is preferably a linear alkyl group. Preferred examples of the cationic surfactant which has an alkyl group comprising 10 or more carbon atoms and has a quaternary ammonium include a cationic surfactant having a structure represented by $CH_3-(CH_2)_n-N^+(CH_3)_3.Br^-$, and $CH_3-(CH_2)_n-N^+(CH_3)_3.Cl^-$ (in both formulae, n is an integer of 9 or greater), specific examples of which include decyltrimethylammonium bromide (C10TAB), dodecyltrimethylammonium bromide (C12TAB), tetradecyltrimethylammonium bromide (C14TAB), hexadecyltrimethylammonium bromide (C16TAB), decyltrimethylammonium chloride (C10TAC), dodecyltrimethylammonium chloride (C12TAC), tetradecyltrimethylammonium chloride (C14TAC), hexadecyltrimethylammonium chloride (C16TAC), and the like.

Among the above-mentioned examples, particularly preferably used is at least one selected from the group consisting of N-dodecyl-N,N-dimethyl-3-ammonio-1-propanesulfonate (C12APS), N-tetradecyl-N,N-dimethyl-3-ammonio-1-propanesulfonate (C14APS), sodium dodecyl sulfate (SDS), sodium N-lauroyl sarcosinate (NLS), dodecylbenzenesulfonate (SBDS), dodecyltrimethylammonium bromide (C12TAB), tetradecyltrimethylammonium bromide (C14TAB), dodecyltrimethylammonium chloride (C12TAC), and tetradecyltrimethylammonium chloride (C14TAC), or at least one selected from the group consisting of N-dodecyl-N,N-dimethyl-3-ammonio-1-propanesulfonate (C12APS), N-tetradecyl-N,N-dimethyl-3-ammonio-1-propanesulfonate (C14APS), sodium dodecyl sulfate (SDS), and sodium N-lauroyl sarcosinate (NLS).

The concentration of a surfactant in a reaction system is not limited as long as the parvovirus B19 antigen and antibody can be simultaneously detected, and may be in the range of, for example, 0.01 to 10%, 0.03 to 7%, 0.05 to 5%, 0.1 to 3%, or 0.5 to 2%. Here, % is % by weight. In cases where a plurality of surfactants having the effect of increasing the sensitivity in a parvovirus B19 antigen-antibody simultaneous detection system are used in combination, the total concentration of the surfactants may be in the above-described ranges.

The simultaneous detection of the parvovirus B19 antigen and antibody according to the present invention is typically carried out by immunoassay. As an immunoassay method, the sandwich method and the competition method can be used, and the sandwich method is preferably used. The sandwich immunoassay itself is a well-known, conventional method. Specific examples thereof include various techniques such as chemiluminescent enzyme immunoassay (CLEIA), enzyme-linked immunosorbent assay (ELISA), radioimmunoassay, and electrochemiluminescence immunoassay, any of which techniques can be used in the present invention.

In the present invention, the term "detect" includes qualitative detection, quantitative detection, and semi-quantitative detection. The term "measure" includes qualitative detection, quantification, and semi-quantification.

As the 1st probe, a molecule which binds specifically to a parvovirus B19 antigen can be used. Typical examples of such specifically binding molecules include antibodies which bind specifically to a parvovirus B19 antigen, or antigen-binding fragments thereof. As the 1st probe, one kind of molecule among such ones can be used, or multiple kinds of such molecules may be used in combination. When an antibody is used as the 1st probe, it may be a polyclonal antibody or a monoclonal antibody, and a monoclonal antibody is preferred from the viewpoints of immunoassay reproducibility and the like.

The 2nd probe may be a molecule to which an anti-parvovirus B19 antibody binds specifically (a 2nd probe-1). Typical examples of such molecules include polypeptides containing the full length or a partial region of a parvovirus B19 antigen, and preferably polypeptides containing a partial region of a parvovirus B19 antigen. The 2nd probe-1 also captures anti-parvovirus B19 antibodies which are not an IgM type antibody, and, for example, when an IgG type anti-parvovirus B19 antibody is present in a sample, the IgG type anti-parvovirus B19 antibody is also captured by the 2nd probe-1. Accordingly, in order to specifically detect an IgM type anti-parvovirus B19 antibody, a step of allowing a molecule that binds specifically to a human IgM type antibody to react with the antibody to be detected, as well as a step of allowing the 2nd probe-1 to react with the antibody to be detected, is required. Typical examples of molecules which bind specifically to a human IgM type antibody include anti-human IgM antibodies or antigen-binding fragments thereof. The anti-human IgM antibody may be a monoclonal antibody or a polyclonal antibody.

As the 2nd probe, a molecule which binds specifically to a human IgM type antibody (a 2nd probe-2) may also be used. Typical examples of such molecules include anti-human IgM antibodies or antigen-binding fragments thereof, as described above. In this mode, in addition to a step of allowing the 2nd probe-2 to react with the antibody to be detected, a step of allowing the above-mentioned molecule to which an anti-parvovirus B19 antibody specifically binds, which may be used as a 2nd probe-1, to react with the antibody to be detected is further carried out. Also when used as the 2nd probe-2, the anti-human IgM antibody may be a monoclonal antibody or a polyclonal antibody.

The present invention can be sufficiently carried out by using at least one of the above-described 2nd probe-1 and the 2nd probe-2 as a 2nd probe. As with the 1st probe, only one kind of molecule may be used as the 2nd probe, or multiple kinds of molecules may be used in combination.

Parvovirus B19 has the structural proteins: VP2, which is the main capsid antigen; and VP1, which is the minor capsid antigen. VP1 has a structure in which the N-terminus of VP2 is expanded. The amino acid sequence of the main capsid antigen VP2 of parvovirus B19 is shown in SEQ ID NO: 1 in the Sequence Listing. The amino acid sequence of VP2 is deposited under Accession No. CB163309.1 in GenBank. The base sequence of parvovirus B19 is deposited under Accession No. FN598217.1 in GenBank. The base sequence shown in SEQ ID NO: 2 is the full length base sequence of parvovirus B19. The base sequence encoding the VP2 antigen (SEQ ID NO: 1) is the base sequence of the 3304th to 4968th bases of SEQ ID NO: 2.

In the present invention, the "parvovirus B19 antigen" includes both VP2 and VP1, and preferably refers to VP2. That is, in the simultaneous detection method according to the present invention, at least one of a VP1 antigen and a VP2 antigen in a sample and at least one of an IgM type anti-VP1 antibody and an IgM type anti-VP2 antibody in the sample may be simultaneously detected, and the simultaneous detection of a VP2 antigen and an IgM type anti-VP2 antibody in the sample is preferred. Examples of the 1st probe capable of binding to VP2 include an anti-VP2 antibody which binds specifically to VP2, or an antigen-binding fragment thereof. Examples of the 2nd probe capable of binding to an IgM type anti-VP2 antibody include a polypeptide containing the full length or a partial region of VP2, and preferably a polypeptide containing a partial region of VP2. When a VP2 antigen and an IgM type anti-VP2 antibody are simultaneously detected using the 2nd probe-2, the detection reaction can be carried out by capturing an IgM type antibody in a sample with the 2nd probe-2, and then allowing the captured antibody to react with, for example, a labeled VP2 polypeptide prepared by attaching a labeling substance to a polypeptide containing the full length or a partial region of VP2.

Methods of producing antibodies and antigen-binding fragments thereof are well-known, conventional methods, per se. An anti-parvovirus B19 polyclonal antibody which binds specifically to VP2 can be obtained by, for example: immunizing an animal (except a human) with the parvovirus main antigen VP2 or a partial fragment thereof, together with an adjuvant when appropriate; obtaining an antiserum from blood collected from the immunized animal; and purifying a polyclonal antibody from the antiserum. The immunization is usually carried out multiple times over a period of several weeks in order to increase the antibody titer in the immunized animal. The antibody in the antiserum can be purified by, for example, fractionation by ammonium sulfate precipitation, fractionation by anion chromatography, affinity column purification, or the like.

An anti-parvovirus B19 monoclonal antibody can be produced by, for example, a well-known hybridoma method. Specifically, an anti-parvovirus B19 monoclonal antibody which binds specifically to VP2 can be obtained by: immunizing an animal (except a human) with the parvovirus B19 main antigen VP2 or a partial fragment thereof, together with an adjuvant when appropriate; collecting antibody-producing cells such as splenic cells or lymphocytes from the immunized animal; fusing these cells with myeloma cells to prepare hybridomas; selecting a hybridoma that produces an antibody which binds to VP2; growing the selected hybridoma; and then collecting the antibody from the culture supernatant.

Anti-human IgM polyclonal and monoclonal antibodies can also be prepared in the same manner as described above, using human IgM or a partial fragment thereof as an immunogen.

In addition, commercially available antibodies can also be used as an anti-parvovirus B19 antibody and anti-human IgM antibody.

The "antigen-binding fragment" may be any antibody fragment as long as it retains the binding capacity to the antigen (antigen-antibody reactivity) the original antibody has. Specific examples thereof include, but are not limited to, Fab, F(ab')$_2$, scFv, and the like. As is well known, Fab and F(ab')$_2$ can be obtained by treating a monoclonal antibody with a proteolytic enzyme such as papain or pepsin. A method of producing scFv (single chain fragment of variable region; single-chain antibody) is also well known. scFv can be obtained, for example, by extracting mRNA from a hybridoma produced as described above to prepare single-stranded cDNA; carrying out PCR using immunoglobulin H chain-specific and L chain-specific primers to amplify the immunoglobulin H chain gene and L chain gene from the single-stranded cDNA; connecting the amplified fragments by a linker; adding thereto appropriate restriction enzyme sites; introducing it into a plasmid vector; transforming *E.*

*coli* with the plasmid vector to express the scFv; and recovering the scFv from *E. coli*.

A polypeptide containing the full length or a partial region of parvovirus B19 antigen can be produced by a conventional method such as a chemical synthesis method or a genetic engineering technique.

Specific examples of the chemical synthesis method include the Fmoc method (the fluorenylmethyloxycarbonyl method), the tBoc method (the t-butyloxycarbonyl method), and the like. Moreover, the synthesis may also be carried out using any of various commercially available peptide synthesizers by a conventional method. In the case of chemical synthesis, a desired polypeptide can be synthesized based only on its amino acid sequence.

Methods of producing a polypeptide by genetic engineering techniques are also well known. When a polypeptide containing the full length or a partial region of VP2 is produced by genetic engineering techniques, the production of the polypeptide may be carried out, for example, as follows. PCR is carried out using the full length VP2 DNA cloned beforehand as a template and using primers designed based on the gene sequence information of VP2 to prepare a polynucleotide that encodes the entire region or a desired portion of VP2. The primers used in PCR can be designed as appropriate based on the base sequence shown in SEQ ID NO: 2, the VP2 sequence information deposited in a database such as GenBank, or the like. Or, a polynucleotide that encodes a desired polypeptide can also be prepared by a conventional method using a commercially available nucleic acid synthesizer. Since codons coding for the respective amino acids are known, if an amino acid sequence can be specified, the base sequence of a polynucleotide encoding the amino acid sequence can also be determined. Then, the prepared polynucleotide is incorporated into an appropriate vector to express the polypeptide in an appropriate expression system, and the expressed polypeptide is recovered, and thereby the desired polypeptide can be obtained. The vectors and various expression systems (bacterial expression system, yeast cell expression system, mammalian cell expression system, insect cell expression system, cell-free expression system, and the like) to be used are also well known, and various vectors, host cells, reagents, and kits are commercially available. Therefore, those skilled in the art can select and use appropriate ones. Human-derived cultured cells are also commercially available or distributed, and thus can be easily obtained.

In the present invention, the length of the "partial region" of a parvovirus B19 antigen is not limited as long as the length is sufficient to allow the antibody to be captured to bind to the region through antigen-antibody reaction. In this art, it is known that polypeptides having a size of about 7 residues can exhibit antigenicity. Accordingly, the partial region can be a region of not less than 7 residues, preferably not less than 10 residues. However, if the size of the partial region is too small, the cross-reaction with unintended antibodies is more likely to occur. Hence, the length of the partial region can be, for example, not less than 30 residues, not less than 40 residues, not less than 50 residues, or not less than 100 residues.

In order to accomplish the simultaneous detection of the parvovirus B19 antigen and antibody, it is necessary to construct the reaction system so that the binding reaction between the 1st probe and the 2nd probe should not occur. For example, in a mode where a VP2 antigen and an IgM type anti-VP2 antibody are simultaneously detected, when a 2nd probe-1 is employed as a 2nd probe, a polypeptide which does not contain any region recognized by an anti-VP2 antibody or antigen-binding fragment thereof used as a 1st probe, is used as the 2nd probe-1. That is, a polypeptide which contains a partial region of VP2 and does not contain a region recognized by a 1st probe is used as a 2nd probe-1. Preferred specific examples of the 1st probe include an antibody which recognizes an epitope contained in the region of the 279th to 388th amino acids of the VP2 antigen, or an antigen-binding fragment thereof. Preferred specific examples of the 2nd probe-1 used in combination with this preferred specific example of the 1st probe include a polypeptide which contains a partial region of VP2 and does not contain the region of the 279th to 388th amino acids of VP2; more specifically, a polypeptide which contains any region selected from the region of the 1st to 278th amino acids of SEQ ID NO: 1, the region of the 389th to 554th amino acids of SEQ ID NO: 1, and partial regions of these regions.

When the simultaneous detection method according to the present invention is carried out by a sandwich immunoassay, a labeled antigen polypeptide as well as a labeled antibody may be used depending on the type of a 2nd probe to be employed, and it is necessary to construct the reaction system so that the binding of the labeled antigen and the labeled antibody with the 1st probe and the 2nd probe should not occur.

The method for simultaneous detection of the human parvovirus B19 antigen and antibody according to the present invention will be specifically described by way of an example hereinbelow, where the method is carried out by a sandwich immunoassay using a 1st probe and a 2nd probe immobilized on a solid phase as solid phase probes. A mode where a 2nd probe-1 is used as a 2nd probe and a mode where a 2nd probe-2 is used as a 2nd probe are separately described.

A. Simultaneous Detection Using 2nd Probe-1

An anti-parvovirus B19 antibody that binds specifically to a parvovirus B19 antigen in a sample (sample antigen) is used as a 1st probe, and a parvovirus B19 antigen polypeptide containing a partial region of the parvovirus B19 antigen (2nd probe-1), to which polypeptide an IgM type anti-parvovirus B19 antibody in a sample (sample antibody) binds specifically, is used as a 2nd probe. First, these probes are immobilized on a solid phase. When a plate is used as a solid phase, the 1st probe and the 2nd probe-1 are immobilized on the same solid phase carrier (on the same well). When particles such as magnetic particles are used as a solid phase, the 1st probe and the 2nd probe-1 may be immobilized on the same solid phase carrier (on the same particle), or the probes may be immobilized on different solid phase carriers (on different particles), respectively, and then the particles are mixed and used.

Then, the solid phase probes are brought into contact with the sample in the presence of a surfactant (primary reaction step). When a plate is used as a solid phase, a sample (which may be diluted with a sample diluent, as appropriate) and a surfactant can be added to the wells comprising the two solid phase probes. When particles are used as a solid phase, particles comprising the two solid phase probes can be mixed with a sample and a surfactant. By these procedures, the parvovirus B19 antigen protein in the sample is captured on the solid phase via the 1st probe, while the anti-parvovirus B19 antibody (which may contain an IgG type anti-parvovirus B19 antibody besides an IgM type anti-parvovirus B19 antibody, if the IgG type anti-parvovirus B19 antibody is also present in the sample) in the sample is captured on the solid phase via the 2nd probe-1.

Next, the components in the sample which have not been captured on the solid phase are removed by washing the solid phase with, for example, a suitable buffer, and then the solid phase is brought into contact with an appropriate probe labeled with a labeling substance, to allow the labeled probe to be bound to each of the sample antigen and the sample antibody captured on the solid phase (secondary reaction step). A labeled probe used in combination with a 1st probe to detect the sample antigen is herein referred to as a 3rd probe for convenience. As a 3rd probe, a probe prepared by attaching a labeled substance to a molecule which binds specifically to the sample antigen at a site other than where the 1st probe binds (typically, an anti-parvovirus B19 antibody which binds to the sample antigen at a site other than where the 1st probe binds) can be used. On the other hand, a labeled probe used in combination with a 2nd probe-1 to detect the sample antibody is herein referred to as a 4th probe-1 for convenience. As a 4th probe-1, a probe prepared by attaching a labeled substance to a molecule which binds specifically to a human IgM type antibody (typically, an anti-human IgM antibody) can be used. A secondary reaction step may be carried out in the presence of or in the absence of a surfactant.

To the 3rd probe and the 4th probe-1, the same labeling substance or different labeling substances may be attached. In the present invention, it is not required to separately detect a parvovirus B19 antigen and an IgM type anti-parvovirus B19 antibody. Therefore, the same labeling substance may be attached to the 3rd probe and the 4th probe-1. For example, ALP may be attached to both probes. When different labeling substances are attached thereto, signals from the respective labeling substances can be distinguished, so that a parvovirus B19 antigen and an IgM type anti-parvovirus B19 antibody can be detected separately from each other.

The 1st probe and the labeled 3rd probe are anti-parvovirus B19 antibodies which bind to the parvovirus B19 antigen at respective different sites, i.e., whose epitopes are different from each other, and neither of them has reactivity with the 2nd probe-1. In other words, a polypeptide used as a 2nd probe-1 does not contain any region recognized by the 1st probe, and does not contain any region recognized by the labeled 3rd probe. An epitope of an antibody can be roughly but sufficiently identified by conventional epitope mapping using short peptides. Thus, an appropriate combination of the probes can be selected by identifying the epitopes of known antibodies or newly prepared antibodies and combining antibodies whose recognition sites do not overlap with each other and with the probe polypeptide.

After the completion of the secondary reaction, the solid phase is washed with, for example, a suitable buffer to remove unreacted components from the reaction system. Then, the signal from the labeling substance is detected by an appropriate method. In this manner, a parvovirus B19 antigen and an IgM type anti-parvovirus B19 antibody contained in a sample can be measured simultaneously.

Although a mode where the primary reaction step is followed by the secondary reaction step is explained hereinabove, the secondary reaction step may be carried out before the primary reaction step (i.e. the reaction between the labeled probe and the sample may precede the primary reaction), or the primary reaction step and the secondary reaction step may be carried out simultaneously.

B. Simultaneous Detection Using 2nd Probe-2

In this mode, an anti-human IgM antibody (2nd probe-2) is used as a 2nd probe. An anti-parvovirus B19 antibody, which is a 1st probe, and an anti-human IgM antibody are immobilized on a solid phase to provide them as solid phase probes, and the solid phase probes are then brought into contact with a sample in the presence of a surfactant (primary reaction step).

As a labeled 3rd probe used in the secondary reaction step, the same probe as used in the above-described mode A can be used. A labeled probe (4th probe-2) used in combination with the 2nd probe-2 to detect a sample antibody is a probe prepared by attaching a labeling substance to a molecule to which an anti-parvovirus B19 antibody binds specifically. For example, a probe prepared by attaching a labeling substance to a polypeptide containing a partial region of a parvovirus B19 antigen is preferably used as a 4th probe-2.

Neither the 1st probe nor the labeled 3rd probe has reactivity with the 4th probe-2. In other words, a polypeptide used as the 4th probe-2 does not contain any region recognized by the 1st probe and does not contain any region recognized by the labeled 3rd probe.

The other conditions and procedures etc. are the same as in the above-described "A. Simultaneous Detection Using 2nd Probe-1".

A solid phase used in an immunoassay is not particularly limited, and the same solid phase used in known immunoassay systems can be used. Specific examples of the solid phase material include, but are not limited to, polystyrene, polyethylene, sepharose, and the like. The physical shape of a solid phase is not essentially important, and various shapes such as a plate shape, a particulate shape, and a membranous shape can be adopted. A solid phase to be used is preferably such one that an antibody can be easily immobilized on the surface thereof and that an immune complex formed during measurement and unreacted components can be easily separated from each other. For example, a plate, magnetic particles, latex particles, beads, a carrier for chromatography, a membrane, and the like can be used. In particular, a plastic plate and magnetic particles used in usual immunoassays are preferred. Magnetic particles made of such a material as described above are most preferably used from the viewpoints of ease of handling, storage, separation, and the like. The probes can be bound to these solid phases by a conventional method well-known to those skilled in the art, and may be bound by physical adsorption or by a covalent bond. For example, a glutaraldehyde method, a periodic acid method, a maleimide method, a pyridyl-disulfide method, and the like can be used. Or, particles to which a probe(s) (antibody, antigen) is/are bound can be obtained by: adding magnetic particles to a buffer to obtain a particle suspension in which the particles are dispersed; adding an appropriate amount of a probe(s) (antibody, antigen) to the particle suspension; stirring the suspension at 20 to 37° C. for about one hour; collecting magnetic particles by magnetic force; and washing the particles with an appropriate buffer. The composition of a buffer to be used may be a general one used for immobilization of antibodies and antigens, and the pH of the buffer may be any value as long as the antibody can be stably present at the pH and as long as immobilization on a solid phase is not inhibited at the pH.

A labeling substance is also not particularly limited, and the same labeling substance used in known immunoassay systems can be used. Specific examples thereof include enzymes, fluorescent substances, chemiluminescent substances, staining substances, and radioactive substances. Examples of the enzyme that can be used include, but are not limited to, known enzymes such as alkaline phosphatase (ALP), peroxidase, β-galactosidase, and the like. In order to provide a measurement system having high detection sensitivity, ALP is desirably used. As explained above, the same labeling substance may be attached to a 3rd probe and a 4th probe (4th probe-1 or 4th probe-2). These labeling substances can be attached to an antibody or an antigen by a conventional method well-known to those skilled in the art. Attachment of a labeling substance is preferably attained via a covalent bond, for which a glutaraldehyde method, a periodic acid method, a maleimide method, a pyridyl-disulfide method, and the like can be used. In the case of labeling of antibodies, for example, an antibody may be treated with pepsin and then subjected to reduction treatment to obtain an antibody fragment, and the antibody fragment may be mixed with maleimidated ALP, to obtain an antibody labeled with a labeling substance.

When an enzyme is used as a labeling substance, an analyte of interest can be measured by: allowing the enzyme to react with a substrate for the enzyme, such as a chromogenic substrate, fluorescent substrate, or luminescent substrate; and measuring the signal generated as a result of the enzyme-substrate reaction to determine the enzyme activity. For example, when ALP is used as a labeling substance, a luminescent substrate such as disodium 3-(4-methoxyspiro(1,2-dioxetane-3,2'-tricyclo[3.3.1.13,7]decan)-4-yl)phenyl phosphate (for example, the tradename AMPPD) can be used.

When biotin or hapten is used as a labeling substance, detection can be carried out using e.g. streptavidin or an anti-hapten antibody to which an enzyme, a fluorescent substance, a chemiluminescent substance, a staining substance, a radioactive substance or the like is attached.

A signal detection method is selected, as appropriate, depending on the type of a labeling substance. For example, a colorimeter or an absorptiometer can be used for a chromogenic signal; a fluorescent photometer can be used for a fluorescent signal; a photocounter can be used for a luminescent signal; and a radiation measure device can be used for a radiation signal.

As a negative control, a sample derived from a healthy individual not previously infected with parvovirus B19 may be subjected to the simultaneous detection method according to the present invention. A signal value obtained from a healthy individual sample and a signal value obtained from a subject sample are compared, and, when the signal value from the subject sample is higher, it is possible to determine that at least one of a parvovirus B19 antigen and an IgM type anti-parvovirus B19 antibody is present in the subject sample (i.e. positive for parvovirus B19). A cut-off value for determination of whether the subject is positive for parvovirus B19 or not may be calculated from signal values measured beforehand in a plurality of healthy individual samples. As a cut-off value, the average value of signal values obtained from negative controls, a value of the average value+2SD (SD: a standard deviation), or the like can be used. When a signal value obtained from a subject sample is equal to or higher than the cut-off value, it is possible to determine that the subject is positive for parvovirus B19. Furthermore, the cut-off value and a signal value obtained from a subject sample may be compared to determine a discriminant value using an appropriate calculating formula. In this case, when the discriminant value is equal to or higher than a predetermined value, it is possible to determine that the subject is positive for parvovirus B19.

Furthermore, a positive control may also be subjected to the simultaneous detection method according to the present invention. As a positive control, a solution that contains, at an appropriate concentration, a sample positive for parvovirus B19 antigen, a recombinant parvovirus B19 antigen, a sample positive for IgM type anti-parvovirus B19 antibody, a purified IgM type anti-parvovirus B19 antibody, an IgM type anti-parvovirus B19 antibody obtained by immunizing another animal species, or a mixture thereof can be used.

The cut-off value can also be set using signal values obtained from a positive control and a negative control. Also in this case, when a signal value obtained from a subject sample is equal to or higher than the cut-off value, it is possible to determine that the subject is positive for parvovirus B19. Further, when a discriminant value is determined and the discriminant value is equal to or higher than a predetermined value, it is possible to determine that the subject is positive for parvovirus B19. Moreover, a positive reference value and a negative reference value may be set from the average value or the like of the signal values obtained from a plurality of positive controls and a plurality of negative controls, and the determination can be carried out in the following manner: the subject is determined to be negative for parvovirus B19 (neither a parvovirus B19 antigen nor an IgM type anti-parvovirus B19 antibody is present in a subject sample) when the signal value of a subject sample is below a negative reference value; the subject is determined to be positive for parvovirus B19 when the signal value of a subject sample is equal to or higher than a positive reference value; and the subject is determined to be suspected of being infected when the signal value of a subject sample is equal to or higher than a negative reference value and below a positive reference value.

A sample to which the antigen-antibody simultaneous detection method according to the present invention is applied is a sample separated from a subject. The sample is not limited and may be any sample as long as it is expected to contain parvovirus B19 antigen and antibody if the subject is infected with parvovirus B19. Preferable specific examples of the sample include whole blood, plasma, and serum. If necessary, the sample may be diluted, as appropriate, and used.

A subject is not limited as long as it is a mammal, and is generally a human. For example, a subject may be a patient infected with parvovirus B19 or a patient suspected of being infected with parvovirus B19.

A kit for simultaneous detection of parvovirus B19 antigen and antibody according to the present invention comprises a 1st probe capable of binding to a parvovirus B19 antigen, a 2nd probe capable of binding to an IgM type anti-parvovirus B19 antibody, and a surfactant. The kit may be for simultaneous detection by an immunoassay, preferably by a sandwich immunoassay. For example, the kit may further comprise a solid phase carrier in a shape of a plate, and may comprise the 1st probe and the 2nd probe in a manner where these probes are immobilized in the same wells of the plate. Or, the kit may further comprise a particulate carrier such as magnetic particles, latex particles, and beads as a solid phase carrier, and may comprise the 1st probe and the 2nd probe in a manner where these probes are immobilized on the same or different carrier particles. In cases where the probes are immobilized on different carrier particles, the particles are mixed and used in the primary reaction step.

Examples

The present invention will be more specifically described below by way of examples. However, the present invention is not limited to the examples below.

(1) Preparation of Recombinant VP2 Antigen

VP2, which is the main component protein of parvovirus, was expressed in the following manner. The full length VP2 DNA which had been cloned beforehand was cut with a restriction enzyme, and incorporated into a Baculovirus Transfer Vector (pAcYM1) that had been cut with the corresponding restriction enzyme. This plasmid was introduced into Sf9 insect cells together with a Baculo Gold Liniarized Baculovirus DNA (made by Pharmagen Limited) by a lipofectin method. After the cells were cultured for several days, virus was collected from the culture supernatant. This virus was cloned using limiting dilution method for virus purification. Sf21 insect cells were allowed to be infected with this purified recombinant virus, and a recombinant protein (VP2) was collected from the cultured insect cells and purified.

Collection and purification of VP2 from the insect cells were carried out in the following manner. The insect cells were collected by centrifugation and subjected to ultrasonic breaking, followed by centrifugation to collect a precipitate. The precipitate was washed, and a crude fraction containing a recombinant VP2 antigen was collected. By preliminarily carrying out slab SDS-PAGE, the concentration of separation gel for SDS-PAGE Model 491 Prep Cell for purification (made by Bio-Rad Laboratories, Inc.) was determined to be 10%, and a cylindrical separation gel was produced. A crude fraction of the recombinant VP2 was dissolved in 2 mL of sample buffer containing SDS at a concentration of 2%, and the resulting mixture was subjected to electrophoresis to collect VP2 eluting from the end of the cylindrical gel. The collected VP2 was concentrated using Centriprep (made by Amicon Corp.) to obtain a recombinant VP2 antigen.

(2) Preparation of Recombinant VP2 Partial Polypeptide

A recombinant VP2 partial polypeptide having a partial sequence of a parvovirus VP2 antigen was expressed in the following manner. PCR was carried out using the full length VP2 DNA which had been cloned beforehand as a template to amplify DNA fragments containing partial sequences of interest (the nucleotide sequence of the 3304th to 4137th nucleotides of SEQ ID NO: 2, and the nucleotide sequence of the 4468th to 4968th nucleotides of SEQ ID NO: 2), and each of the DNA fragments was cloned in an expression vector pETBA (BioDynamics Laboratory, Inc.). The obtained plasmids for expression were introduced into *E. coli*, respectively, to induce expression of VP2 partial polypeptides. Thereafter, the *E. coli* cells were collected by centrifugation and subjected to ultrasonic breaking, followed by centrifugation to collect precipitates. The precipitates were washed, and crude fractions each containing a recombinant VP2 partial polypeptide were collected. The crude fractions were purified through a gel filtration column to obtain a recombinant VP2 partial polypeptide 1 containing the amino acid sequence of the 1st to 278th amino acids of SEQ ID NO: 2 and a recombinant VP2 partial polypeptide 2 containing the amino acid sequence of the 389th to 554th amino acids of SEQ ID NO: 2.

(3) Establishment of Anti-VP2 Monoclonal Antibodies

BALB/c mice were immunized with the recombinant VP2 antigen obtained in the above-described (1), and the spleen lymphocytes of the immunized mice and myeloma cells were fused to produce an anti-VP2 monoclonal antibody. That is, the recombinant VP2 antigen emulsified with Freund's complete adjuvant was administered at 25 to 100 μg/mouse for the initial immunization, and two weeks later, the mice were additionally immunized with the same antigen emulsified with Freund's incomplete adjuvant. About two weeks thereafter, the recombinant VP2 antigen dissolved in physiological saline was intravenously administered to the mice, and 3 to 4 days later, the spleens were taken out to prepare splenic cells. Mouse myeloma cells (P3U1) which had been cultured beforehand in an RPMI-1640 culture medium were mixed with the splenic cells at a ratio of 1:2 to 1:5, and the cells were fused using polyethylene glycol. The fused cells were floated in an HAT medium containing hypoxanthine, aminopterin and thymidine, then dispensed in a 96-well culture plate, and cultured in a $CO_2$ incubator at 37° C.

Then, part of the culture supernatant was taken up and subjected to ELISA using a 96-well ELISA plate in which the recombinant VP2 antigen prepared in the above-described (1) were solid-phased, thereby screening the wells of the plate for those producing the anti-VP2 antibody, to obtain a plurality of hybridomas that produced monoclonal antibodies having reactivity with VP2. The obtained hybridomas were single cloned in accordance with a conventional limiting dilution method to obtain three kinds of anti-VP2 antibody (VP2-1, VP2-2, VP2-3)-producing hybridomas.

(4) Production of Monoclonal Antibodies

Mice received preliminary intraperitoneal administration of 0.5 mL of pristane, and the hybridomas obtained in the above-described (3) were transplanted in the abdominal cavities of the mice at about $1 \times 10^7$ cells per mouse, to obtain each monoclonal antibody generated in the ascitic fluid. The monoclonal antibodies were purified by separating IgG fractions through a Sepharose column comprising protein A bound thereto (produced by Bio-Rad Laboratories, Inc.).

Next, the obtained monoclonal antibodies were each tested for reactivity with each polypeptide, using a peptide mapping for polypeptides consisting of 20 to 30 amino acids. Obtained results confirmed that the monoclonal antibody VP2-1 is an antibody which recognizes an epitope contained in the amino acid sequence of the 279th to 298th amino acids of SEQ ID NO: 1, that the monoclonal antibody VP2-2 is an antibody which recognizes an epitope contained in the amino acid sequence of the 329th to 358th amino acids of SEQ ID NO: 1, and that the monoclonal antibody VP2-3 is an antibody which recognizes an epitope contained in the amino acid sequence of the 359th to 388th amino acids of SEQ ID NO: 1.

(5) Preparation of Labeled Monoclonal Antibodies

A mouse anti-human IgM monoclonal antibody and alkaline phosphatase from bovine small intestine (produced by Oriental Yeast Co., Ltd.) were bound together by the method of Yoshitake et al. (Yoshitake et al., J. Biochem. 1982, 92(5), p. 1413-1424) to prepare an ALP-enzyme-labeled anti-human IgM monoclonal antibody.

Specifically, a desalted mouse anti-human IgM monoclonal antibody (the final concentration: 3 mg/mL) and pepsin (the final concentration: 6 μg/mL) were mixed in a 0.1 M citric acid buffer (pH 3.5), and the resulting mixture was allowed to stand at 37° C. for 1 hour for pepsin digestion. After the reaction was terminated, the mixture was subjected to the purification by gel filtration to obtain an antibody with no Fc region. Next, 2-mercaptoethanol (the final concentration: 10 mM) was added thereto, and the resulting mixture was allowed to stand at 37° C. for 3 hours for thiolation. The mixture was further desalted to obtain an Fab' of the mouse anti-human IgM monoclonal antibody.

On the other hand, the desalted alkaline phosphatase and N-(4-maleimido butylyloxy)-succinimide (GMBS) (the final concentration: 0.3 mg/mL) were mixed together, and the resulting mixture was allowed to stand at 30° C. for 1 hour for maleimidization.

After desalting, the Fab' and the maleimidized alkaline phosphatase were mixed at a molar ratio of 1:1, and allowed to stand at 25° C. for 30 minutes for coupling. To the coupling solution, 2-mercaptoethanol (the final concentration: 10 mM) was added. The resulting mixture was allowed to stand at 4° C. overnight, and then the reaction was terminated. After the solution was concentrated and desalted, 100 mM MES (pH 6.8) containing 1% BSA, 1 mM NaCl, and 0.1 mM $ZnCl_2$ was added to the solution to prepare a 200 μg/mL solution of an ALP-labeled anti-human IgM monoclonal antibody.

The anti-VP2 monoclonal antibody VP2-1 was also treated in the same manner to obtain an ALP-labeled anti-VP2 monoclonal antibody VP2-1.

(6) Establishment of Sandwich ELISA for Simultaneous Measurement of Parvovirus B19 Antigen and Anti-Parvovirus B19 Antibody, and Evaluation of Addition of Amphoteric Surfactant and Anionic Surfactant To an ELISA plate manufactured by NUNC, 100 μL of PBS (pH 7.4) containing the recombinant VP2 partial polypeptides 1 and 2 at 2 μg/mL and VP2-2 and VP2-3 antibodies at 1 μg/mL was added per well, and the plate was incubated at 4° C. overnight. Thereafter, each well was washed with 350 μL of PBS three times, and a blocking solution (PBS containing 0.5% casein, 3% sucrose, and 0.05% ProClin) was added at 300 μL/well, followed by incubation at room temperature for 2 hours. After washing, 100 μL of a sample diluted 20-fold with a primary reaction solution containing a surfactant as shown in Table 1 and Table 2 below (each surfactant was added at a final concentration of 0.5% to PBS containing 1% BSA, 0.05% casein, and 0.05% ProClin) was add to each well, and the plate was incubated at 37° C. for 1 hour. Thereafter, each well was washed with 300 μL of a washing fluid (PBS containing 0.1% Tween 20), and 100 μL of a secondary reaction solution (PBS containing 1% BSA, 0.05% casein, and 0.05% ProClin) containing 1 μg/mL of the ALP-labeled anti-VP2 monoclonal antibody VP2-1 and 0.5 μg/mL of an ALP-labeled anti-IgM monoclonal antibody was added to each well, and the plate was incubated at 37° C. for 1 hour. Thereafter, each well was washed with 300 μL of a washing fluid, and 100 μL of a substrate solution prepared by diluting one tablet of PNPP Substrate Tablets (produced by Thermo Fisher Scientific Inc.) with 5 mL of a diluent (0.1 M carbonic acid buffer, 2.0 mM $MgCl_2$, pH 9.8) was added to each well. After incubation at 37° C. for 30 minutes, 50 μL of 1 N NaOH was added to each well to terminate the reaction. The absorbance (A415/630 nm) of each well was measured with a spectrophotometer.

Purchased samples were used as positive samples. The IgM titer and IgG titer of the anti-parvovirus B19 antibody and the DNA level (IU/mL) of parvovirus B19 measured in each positive sample are shown in Table 1 and Table 2.

Measurement was also carried out in the same manner using each surfactant in a plurality of negative samples, and the average counts of negative samples and its SD were calculated for each surfactant. The cut-off value for determination of whether a sample was positive or not was set to a value of "the average counts of negative samples+2SD". Since the cut-off value varies depending on which surfactant was added, we set the cut-off value for each surfactant. Furthermore, the counts measured in each positive sample was divided by the cut-off value, and the resulting value was used as a discriminant value. When this discriminant value is 1 or more, it is possible to determine that at least one of a parvovirus B19 antigen and an anti-parvovirus B19 antibody is present in the sample (positive for parvovirus B19).

The results are shown in Table 1 and Table 2. The discriminant values calculated under each condition where each surfactant was added are shown in Table 1 and Table 2. The effect achieved by addition of a surfactant was judged by the percentage obtained by dividing the discriminant value calculated from a sample with addition of a surfactant by the discriminant value calculated from a sample without addition of a surfactant. Increase in detection sensitivity was observed in multiple samples by addition of an amphoteric surfactant or an anionic surfactant to the reaction solution as compared to the condition where no surfactant was added. In particular, addition of C12APS or C14APS resulted in a remarkable increase in detection sensitivity. Addition of SDS or NLS also resulted in a large increase in detection sensitivity.

TABLE 1

|  |  | IgM Titer | IgG Titer | DNA | No addition Control | Amphoteric (Concentration 0.5%) | |
|---|---|---|---|---|---|---|---|
|  |  |  |  |  |  | C12APS | C14APS |
| Cut-Off Value |  |  |  |  | 0.058 | 0.073 | 0.075 |
| Counts | PVP201-07 | 7.5 | 0.6 | 1.1*10^4 | 0.102 | 2.548 | 2.344 |
|  | PVP201-09 | 5.5 | 2.6 | 4.9*10^5 | 0.125 | 0.792 | 0.795 |
|  | PVP201-11 | 4.4 | 0.8 | 3.7*10^4 | 0.050 | 0.608 | 0.565 |
|  | PVP201-12 | 6.2 | 0.3 | 2.5*10^6 | 0.084 | 0.586 | 0.522 |
|  | PVP201-13 | 2.4 | 0.1 | 2.3*10^9 | 0.055 | 0.190 | 0.180 |
|  | PVP201-15 | 0.9 | 0.1 | 2.9*10^10 | 0.047 | 0.109 | 0.100 |
|  | PVP201-16 | 0.1 | 0 | 4.4*10^11 | 0.083 | 0.112 | 0.115 |
| Discriminant Value | PVP201-07 | 7.5 | 0.6 | 1.1*10^4 | 1.8 | 34.9 | 31.3 |
|  | PVP201-09 | 5.5 | 2.6 | 4.9*10^5 | 2.2 | 10.8 | 10.6 |
|  | PVP201-11 | 4.4 | 0.8 | 3.7*10^4 | 0.9 | 8.3 | 7.5 |
|  | PVP201-12 | 6.2 | 0.3 | 2.5*10^6 | 1.4 | 8.0 | 7.0 |
|  | PVP201-13 | 2.4 | 0.1 | 2.3*10^9 | 0.9 | 2.6 | 2.4 |
|  | PVP201-15 | 0.9 | 0.1 | 2.9*10^10 | 0.8 | 1.5 | 1.3 |
|  | PVP201-16 | 0.1 | 0 | 4.4*10^11 | 1.4 | 1.5 | 1.5 |
| Discriminant Value from Addition of Surfactant/ Discriminant Value from No Addition (%) | PVP201-07 | 7.5 | 0.6 | 1.1*10^4 |  | 1938.9 | 1738.9 |
|  | PVP201-09 | 5.5 | 2.6 | 4.9*10^5 |  | 490.9 | 481.8 |
|  | PVP201-11 | 4.4 | 0.8 | 3.7*10^4 |  | 922.2 | 833.3 |
|  | PVP201-12 | 6.2 | 0.3 | 2.5*10^6 |  | 571.4 | 500.0 |
|  | PVP201-13 | 2.4 | 0.1 | 2.3*10^9 |  | 288.9 | 266.7 |
|  | PVP201-15 | 0.9 | 0.1 | 2.9*10^10 |  | 187.5 | 162.5 |
|  | PVP201-16 | 0.1 | 0 | 4.4*10^11 |  | 107.1 | 107.1 |

TABLE 2

|  |  | IgM Titer | IgG Titer | DNA | No Addition Control | Anion (0.5%) SDS | NLS |
|---|---|---|---|---|---|---|---|
| Cut-Off Value |  |  |  |  | 0.058 | 0.166 | 0.096 |
| Counts | PVP201-07 | 7.5 | 0.6 | 1.1*10^4 | 0.102 | 1.998 | 1.416 |
|  | PVP201-09 | 5.5 | 2.6 | 4.9*10^5 | 0.125 | 0.873 | 0.363 |
|  | PVP201-11 | 4.4 | 0.8 | 3.7*10^4 | 0.050 | 0.620 | 0.251 |
|  | PVP201-12 | 6.2 | 0.3 | 2.5*10^6 | 0.084 | 0.656 | 0.236 |
|  | PVP201-13 | 2.4 | 0.1 | 2.3*10^9 | 0.055 | 0.267 | 0.134 |
|  | PVP201-15 | 0.9 | 0.1 | 2.9*10^10 | 0.047 | 0.120 | 0.073 |
|  | PVP201-16 | 0.1 | 0 | 4.4*10^11 | 0.083 | 0.508 | 0.333 |
| Discriminant Value | PVP201-07 | 7.5 | 0.6 | 1.1*10^4 | 1.8 | 12.0 | 14.8 |
|  | PVP201-09 | 5.5 | 2.6 | 4.9*10^5 | 2.2 | 5.3 | 3.8 |
|  | PVP201-11 | 4.4 | 0.8 | 3.7*10^4 | 0.9 | 3.7 | 2.6 |
|  | PVP201-12 | 6.2 | 0.3 | 2.5*10^6 | 1.4 | 4.0 | 2.5 |
|  | PVP201-13 | 2.4 | 0.1 | 2.3*10^9 | 0.9 | 1.6 | 1.4 |
|  | PVP201-15 | 0.9 | 0.1 | 2.9*10^10 | 0.8 | 0.7 | 0.8 |
|  | PVP201-16 | 0.1 | 0 | 4.4*10^11 | 1.4 | 3.1 | 3.5 |
| Discriminant Value from Addition of Surfactant/ Discriminant Value from No Addition (%) | PVP201-07 | 7.5 | 0.6 | 1.1*10^4 |  | 666.7 | 822.2 |
|  | PVP201-09 | 5.5 | 2.6 | 4.9*10^5 |  | 240.9 | 172.7 |
|  | PVP201-11 | 4.4 | 0.8 | 3.7*10^4 |  | 411.1 | 288.9 |
|  | PVP201-12 | 6.2 | 0.3 | 2.5*10^6 |  | 285.7 | 178.6 |
|  | PVP201-13 | 2.4 | 0.1 | 2.3*10^9 |  | 177.8 | 155.6 |
|  | PVP201-15 | 0.9 | 0.1 | 2.9*10^10 |  | 87.5 | 100.0 |
|  | PVP201-16 | 0.1 | 0 | 4.4*10^11 |  | 221.4 | 250.0 |

(7) Evaluation of Addition Concentration of Amphoteric Surfactant (C12APS)

Next, the addition concentration of C12APS was evaluated. Measurements were made in the same manner as in the above-described (6). The results are shown in Table 3. In the Table, the "vs. No Addition" represents discriminant value from addition of surfactant/discriminant value from no addition (%) (the same applies to Table 4 to Table 10). Increase in detection sensitivity was observed across the addition concentrations tested, from 0.05% to 5.0%, as compared to the no addition condition.

TABLE 3

|  |  | No Addition Control | 0.05% C12APS | 0.1% C12APS | 0.5% C12APS | 1.0% C12APS | 2.0% C12APS | 3.0% C12APS | 4.0% C12APS | 5.0% C12APS |
|---|---|---|---|---|---|---|---|---|---|---|
| Cut-Off Value |  | 0.043 | 0.038 | 0.048 | 0.064 | 0.059 | 0.062 | 0.056 | 0.053 | 0.047 |
| Counts | PVP201-07 | 0.115 | 0.146 | 0.448 | 1.756 | 1.508 | 1.001 | 0.658 | 0.422 | 0.375 |
|  | PVP201-11 | 0.049 | 0.047 | 0.093 | 0.524 | 0.494 | 0.330 | 0.244 | 0.186 | 0.177 |
|  | PVP201-15 | 0.036 | 0.034 | 0.038 | 0.088 | 0.083 | 0.064 | 0.055 | 0.046 | 0.046 |
|  | PVP201-16 | 0.083 | 0.067 | 0.093 | 0.120 | 0.113 | 0.129 | 0.116 | 0.109 | 0.096 |
| Discriminant Value | PVP201-07 | 2.7 | 3.8 | 9.3 | 27.4 | 25.6 | 16.1 | 11.8 | 8.0 | 8.0 |
|  | PVP201-11 | 1.1 | 1.2 | 1.9 | 8.2 | 8.4 | 5.3 | 4.4 | 3.5 | 3.8 |
|  | PVP201-15 | 0.8 | 0.9 | 0.8 | 1.4 | 1.4 | 1.0 | 1.0 | 0.9 | 1.0 |
|  | PVP201-16 | 1.9 | 1.8 | 1.9 | 1.9 | 1.9 | 2.1 | 2.1 | 2.1 | 2.0 |
| vs. No Addition | PVP201-07 |  | 140.7 | 344.4 | 1014.8 | 948.1 | 596.3 | 437.0 | 296.3 | 296.3 |
|  | PVP201-11 |  | 109.1 | 172.7 | 745.5 | 763.6 | 481.8 | 400.0 | 318.2 | 345.5 |
|  | PVP201-15 |  | 112.5 | 100.0 | 175.0 | 175.0 | 125.0 | 125.0 | 112.5 | 125.0 |
|  | PVP201-16 |  | 94.7 | 100.0 | 100.0 | 100.0 | 110.5 | 110.5 | 110.5 | 105.3 |

(8) Evaluation of Addition Concentration of Anionic Surfactant (NLS)

The addition concentration of NLS was evaluated. Measurements were made in the same manner as in the above-described (6) except that a blocking solution (PBS containing 2.0% BSA, 3% sucrose, and 0.05% ProClin), a primary reaction solution (PBS containing 2% BSA and 0.1% ProClin), and a secondary reaction solution (PBS containing 2% BSA and 0.1% ProClin) were used. The results are shown in Table 4. Increase in detection sensitivity was observed almost across the addition concentrations tested, from 0.05% to 5.0%, as compared to the no addition condition.

TABLE 4

|  |  | No Addition Control | 0.05% NLS | 0.1% NLS | 0.5% NLS | 1.0% NLS | 5.0% NLS |
|---|---|---|---|---|---|---|---|
| Cut-Off Value |  | 0.127 | 0.118 | 0.130 | 0.113 | 0.114 | 0.086 |
| Counts | PVP201-07 | 0.516 | 0.552 | 0.594 | 0.936 | 0.624 | 0.174 |
|  | PVP201-16 | 0.336 | 0.366 | 0.414 | 0.486 | 0.528 | 0.552 |
| Discriminant | PVP201-07 | 4.1 | 4.7 | 4.6 | 8.3 | 5.5 | 2.0 |
| Value | PVP201-16 | 2.6 | 3.1 | 3.2 | 4.3 | 4.6 | 6.4 |
| vs. No Addition | PVP201-07 |  | 114.6 | 112.2 | 202.4 | 134.1 | 48.8 |
|  | PVP201-16 |  | 119.2 | 123.1 | 165.4 | 176.9 | 246.2 |

(9) Evaluation of Addition of Amphoteric Surfactants and Anionic Surfactants

Amphoteric surfactants containing an alkyl group and a quaternary ammonium in the molecule was further evaluated for the chain length of the alkyl group. Measurements were made in the same manner as in the above-described (6). The results are shown in Table 5 and Table 6. Increase in detection sensitivity was observed by addition of C10APS or C16APS to the reaction solution as compared to the condition where no surfactant was added, by which the fact that amphoteric surfactants having a C10 or more alkyl group had an effect to increase the detection sensitivity was shown.

Furthermore, the effect obtained when the anionic surfactant SDBS having a C12 alkyl group and the anionic surfactant NDS having a C9 alkyl group were added was evaluated. Measurements were made in the same manner as in the above-described (6). The results are shown in Table 6 and Table 7. Increase in detection sensitivity was observed by addition of SDBS or NDS to the reaction solution as compared to the condition where no surfactant was added, by which the fact that anionic surfactants having a C9 or more alkyl group had an effect to increase the detection sensitivity was confirmed.

TABLE 5

|  |  | No Addition Control | 0.5% C10APS | 0.5% C8APS |
|---|---|---|---|---|
| Cut-Off Value |  | 0.043 | 0.037 | 0.036 |
| Counts | PVP201-07 | 0.115 | 0.133 | 0.099 |
|  | PVP201-16 | 0.083 | 0.064 | 0.077 |
| Discriminant Value | PVP201-07 | 2.7 | 3.6 | 2.8 |
|  | PVP201-16 | 1.9 | 1.7 | 2.1 |
| vs. No Addition | PVP201-07 |  | 133.3 | 103.7 |
|  | PVP201-16 |  | 89.5 | 110.5 |

TABLE 6

|  |  | No Addition Control | 0.5% C16APS | 0.5% SDBS |
|---|---|---|---|---|
| Cut-Off Value |  | 0.038 | 0.042 | 0.077 |
| Counts | PVP201-07 | 0.105 | 0.209 | 0.371 |
|  | PVP201-16 | 0.081 | 0.095 | 0.416 |
| Discriminant Value | PVP201-07 | 2.8 | 5.0 | 9.3 |
|  | PVP201-16 | 2.1 | 2.3 | 10.4 |
| vs. No Addition | PVP201-07 |  | 178.6 | 290.6 |
|  | PVP201-16 |  | 109.5 | 416.0 |

TABLE 7

|  |  | No Addition Control | NDS 0.5% |
|---|---|---|---|
| Cut-Off Value |  | 0.105 | 0.117 |
| Counts | PVP201-07 | 0.124 | 0.187 |
|  | PVP201-16 | 0.143 | 0.295 |
| Discriminant Value | PVP201-07 | 1.2 | 1.6 |
|  | PVP201-16 | 1.4 | 2.5 |
| vs. No Addition | PVP201-07 |  | 133.3 |
|  | PVP201-16 |  | 178.6 |

(10) Evaluation of Addition of Cationic Surfactants

The effect obtained when a cationic surfactant was added was evaluated. Measurements were made in the same manner as in the above-described (8). The results are shown in Table 8. Increase in detection sensitivity was observed in multiple samples by addition of a cationic surfactant to the reaction solution as compared to the condition where no surfactant was added.

TABLE 8

|  |  | No Addition Control | 0.5% C12TAB | 0.5% C14TAB | 0.5% C14TAC |
|---|---|---|---|---|---|
| Cut-Off Value |  | 0.134 | 0.081 | 0.050 | 0.057 |
| Counts | PVP201-07 | 0.326 | 0.150 | 0.174 | 0.189 |
|  | PVP201-11 | 0.095 | 0.059 | 0.054 | 0.058 |
|  | PVP201-15 | 0.091 | 0.081 | 0.066 | 0.074 |
|  | PVP201-16 | 0.349 | 0.710 | 0.460 | 0.465 |
| Discriminant Value | PVP201-07 | 2.4 | 1.9 | 3.5 | 3.3 |
|  | PVP201-11 | 0.7 | 0.7 | 1.1 | 1.0 |
|  | PVP201-15 | 0.7 | 1.0 | 1.3 | 1.3 |
|  | PVP201-16 | 2.6 | 8.8 | 9.2 | 8.2 |
| vs. No Addition | PVP201-07 |  | 79.2 | 145.8 | 137.5 |
|  | PVP201-11 |  | 100.0 | 157.1 | 142.9 |
|  | PVP201-15 |  | 142.9 | 185.7 | 185.7 |
|  | PVP201-16 |  | 338.5 | 353.8 | 315.4 |

(11) Evaluation of Addition Concentration of Cationic Surfactant (C12TAB)

The addition concentration of C12TAB was evaluated. Measurements were made in the same manner as in the above-described (10). The results are shown in Table 9. Because cationic surfactants exerted a high improvement effect in a sample with a high DNA titer (PVP201-16), evaluations were made using the sample PVP201-16. As a result, increase in detection sensitivity was observed across the addition concentrations tested, from 0.05% to 5.0%, as compared to the no addition condition.

TABLE 9

|  |  | No Addition Control | 0.05% C12TAB | 0.1% C12TAB | 0.5% C12TAB | 1.0% C12TAB | 5.0% C12TAB |
| --- | --- | --- | --- | --- | --- | --- | --- |
| Cut-Off Value |  | 0.127 | 0.097 | 0.102 | 0.073 | 0.092 | 0.096 |
| Counts | PVP201-16 | 0.336 | 0.738 | 0.792 | 0.954 | 2.316 | 1.548 |
| Discriminant Value | PVP201-16 | 2.6 | 7.6 | 7.8 | 13.1 | 25.2 | 16.1 |
| vs. No Addition | PVP201-16 |  | 292.3 | 300.0 | 503.8 | 969.2 | 619.2 |

(12) Evaluation of Addition of Nonionic Surfactant (Triton (Registered Trademark), Tween)

The effect obtained when a nonionic cationic surfactant was added was evaluated. Measurements were made in the same manner as in the above-described (6). The results are shown in Table 10. The detection sensitivity under the condition where a nonionic cationic surfactant was added was at the same level as that under the no addition condition, and increase in detection sensitivity was not observed.

TABLE 10

|  |  | No Add. Control | 0.5% Triton 100 | 0.5% Triton 705 | 0.5% Tween 20 | 0.5% Tween 40 | 0.5% Tween 60 | 0.5% Tween 80 |
| --- | --- | --- | --- | --- | --- | --- | --- | --- |
| Cut-Off Value |  | 0.038 | 0.039 | 0.036 | 0.040 | 0.037 | 0.041 | 0.040 |
| Counts | PVP201-07 | 0.105 | 0.096 | 0.090 | 0.106 | 0.108 | 0.108 | 0.106 |
|  | PVP201-15 | 0.044 | 0.043 | 0.043 | 0.044 | 0.046 | 0.043 | 0.043 |
|  | PVP201-16 | 0.081 | 0.079 | 0.078 | 0.078 | 0.079 | 0.090 | 0.079 |
| Discriminant Value | PVP201-07 | 2.8 | 2.5 | 2.5 | 2.7 | 2.9 | 2.6 | 2.7 |
|  | PVP201-15 | 1.2 | 1.1 | 1.2 | 1.1 | 1.2 | 1.0 | 1.1 |
|  | PVP201-16 | 2.1 | 2.0 | 2.2 | 2.0 | 2.1 | 2.2 | 2.0 |
| vs. No Add. | PVP201-07 |  | 89.3 | 89.3 | 96.4 | 103.6 | 92.9 | 96.4 |
|  | PVP201-15 |  | 91.7 | 100.0 | 91.7 | 100.0 | 83.3 | 91.7 |
|  | PVP201-16 |  | 95.2 | 104.8 | 95.2 | 100.0 | 104.8 | 95.2 |

The invention claimed is:

1. A method of simultaneously detecting at least one parvovirus B19 antigen and at least one IgM type anti-parvovirus B19 antibody present in a sample, the method comprising bringing the sample into contact with
   (1) a 1st probe for detecting the parvovirus B19 antigen, and
   (2) a 2nd probe for detecting the IgM type anti-parvovirus B19 antibody, in the presence of at least one surfactant selected from the group consisting of an anionic surfactant, an amphoteric surfactant, and a cationic surfactant within the same reaction.

2. The method according to claim 1, wherein: the anionic surfactant is an anionic surfactant having an alkyl group comprising 9 or more carbon atoms in the molecule; the amphoteric surfactant is an amphoteric surfactant having an alkyl group comprising 10 or more carbon atoms and a quaternary ammonium in the molecule; and the cationic surfactant is a cationic surfactant having an alkyl group comprising 10 or more carbon atoms and a quaternary ammonium in the molecule.

3. The method according to claim 2, wherein: the anionic surfactant is an anionic surfactant having an alkyl group comprising 11 or more carbon atoms in the molecule; the amphoteric surfactant is an amphoteric surfactant having an alkyl group comprising 12 or more carbon atoms and a quaternary ammonium in the molecule; and the cationic surfactant is a cationic surfactant having an alkyl group comprising 12 or more carbon atoms and a quaternary ammonium in the molecule.

4. The method according to claim 2, wherein the surfactant is at least one selected from the group consisting of sodium dodecyl sulfate, sodium N-decanoyl sarcosinate, sodium N-lauroyl sarcosinate, sodium N-myristoyl sarcosinate, dodecylbenzenesulfonate, N-decyl-N,N-dimethyl-3-ammonio-1-propanesulfonate, N-dodecyl-N,N-dimethyl-3-ammonio-1-propanesulfonate, N-tetradecyl-N,N-dimethyl-3-ammonio-1-propanesulfonate, N-hexadecyl-N,N-dimethyl-3-ammonio-1-propanesulfonate, decyltrimethylammonium bromide, dodecyltrimethylammonium bromide, tetradecyltrimethylammonium bromide, hexadecyltrimethylammonium bromide, decyltrimethylammonium chloride, dodecyltrimethylammonium chloride, tetradecyltrimethylammonium chloride, and hexadecyltrimethylammonium chloride.

5. The method according to any one of claims 1 and 2 to 4,
   wherein the method is carried out by an immunoassay, wherein the 1st probe comprises at least one antibody which binds specifically to a parvovirus B19 antigen or an antigen-binding fragment thereof, and wherein the 2nd probe comprises at least one selected from: a polypeptide which contains the full length or a partial region of parvovirus B19 antigen and does not contain a region recognized by the 1st probe; and an anti-human IgM antibody which binds specifically to a human IgM type antibody or an antigen-binding fragment thereof.

6. The method according to claim 5, wherein the immunoassay is a sandwich immunoassay.

7. The method according to claim 5, wherein the 2nd probe comprises at least one polypeptide containing the full length or a partial region of the parvovirus B19 antigen.

8. The method according to claim 5, wherein the parvovirus B19 antigen is VP2.

9. The method according to claim 1, wherein the 1st probe and the 2nd probe are used as solid phase probes immobilized on the same solid phase carrier or different solid phase carriers.

10. The method according to claim 9, wherein the 2nd probe is at least one polypeptide containing a partial region of the parvovirus B19 antigen, and wherein the method comprises bringing the sample into contact with the solid phase probes, and thereafter bringing the solid phase into contact with a labeled anti-parvovirus B19 antibody or an antigen-binding fragment thereof which binds to the parvovirus B19 antigen at a site other than where the 1st probe binds, and a labeled anti-human IgM antibody or an antigen-binding fragment thereof which binds specifically to a human IgM type antibody.

11. The method according to claim 10, wherein the 2nd probe does not contain a region recognized by the 1st probe and does not contain a region recognized by the labeled anti-parvovirus B19 antibody or an antigen-binding fragment thereof.

12. The method according to claim 9, wherein the 2nd probe is anti-human IgM antibody or an antigen-binding fragment thereof and wherein the method comprises bringing the sample into contact with the solid phase probes and thereafter bringing the solid phase into contact with a labeled anti-parvovirus B19 antibody or an antigen-binding fragment thereof which binds to the parvovirus B19 antigen at a site other than where the 1st probe binds, and a labeled polypeptide containing a partial region of the parvovirus B19 antigen.

13. The method according to claim 12, wherein the labeled polypeptide does not contain a region recognized by the 1st probe and does not contain a region recognized by the labeled anti-parvovirus B19 antibody or an antigen-binding fragment thereof.

14. The method according to claim 1, wherein the sample is blood, serum, or plasma.

15. A kit for simultaneous detection of a parvovirus B19 antigen and an IgM type anti-parvovirus B19 antibody, which is used in the method according to claim 1 and comprises a 1st probe for detecting a parvovirus B19 antigen, a 2nd probe for detecting an IgM type anti-parvovirus B19 antibody, and at least one surfactant selected from the group consisting of an anionic surfactant, an amphoteric surfactant, and a cationic surfactant.

* * * * *